(12) United States Patent
Kobayashi et al.

(10) Patent No.: US 12,106,847 B2
(45) Date of Patent: Oct. 1, 2024

(54) ANNOTATION SUPPORT APPARATUS, ANNOTATION SUPPORT METHOD, AND ANNOTATION SUPPORT PROGRAM

(71) Applicants: NATIONAL CANCER CENTER, Tokyo (JP); FUJIFILM Corporation, Tokyo (JP)

(72) Inventors: Kazuma Kobayashi, Tokyo (JP); Mototaka Miyake, Tokyo (JP); Ryuji Hamamoto, Tokyo (JP)

(73) Assignees: NATIONAL CANCER CENTER, Tokyo (JP); FUJIFILM Corporation, Tokyo (JP)

( * ) Notice: Subject to any disclaimer, the term of this patent is extended or adjusted under 35 U.S.C. 154(b) by 310 days.

(21) Appl. No.: 17/381,200

(22) Filed: Jul. 21, 2021

(65) Prior Publication Data
US 2021/0350908 A1 Nov. 11, 2021

Related U.S. Application Data

(63) Continuation of application No. PCT/JP2020/002603, filed on Jan. 24, 2020.

(30) Foreign Application Priority Data

Jan. 24, 2019 (JP) ................................. 2019-010287

(51) Int. Cl.
*G16H 30/40* (2018.01)
*G06F 3/0486* (2013.01)
(Continued)

(52) U.S. Cl.
CPC ........... *G16H 30/40* (2018.01); *G06F 3/0486* (2013.01); *G16H 30/20* (2018.01); *G16H 50/20* (2018.01)

(58) Field of Classification Search
CPC .......... G16H 30/20; G16H 30/40; G16H 50/20
(Continued)

(56) References Cited

U.S. PATENT DOCUMENTS

| 8,630,975 B1* | 1/2014 | Guo | G06N 20/00 |
| | | | 707/726 |
| 2008/0235055 A1* | 9/2008 | Mattingly | G16H 10/40 |
| | | | 705/2 |

(Continued)

FOREIGN PATENT DOCUMENTS

| JP | 2010279542 | 12/2010 |
| JP | 2013132514 | 7/2013 |

(Continued)

OTHER PUBLICATIONS

Dimitrovski et al: Hierarchical annotation of medical images Pattern Recognition, vol. 44, No. 10-11, Mar. 29, 2011 (Mar. 29, 2011), pp. 2436-2449, XP055162305, ISSN: 0031-3203, DOI: 10.1016/j.patcog.2011.03.026 (Year: 2011).*

(Continued)

*Primary Examiner* — Linh Giang Le
(74) *Attorney, Agent, or Firm* — JCIPRNET

(57) ABSTRACT

An annotation support apparatus manages a medical image on the basis of an attribute of each medical image, using a hierarchical structure that has one medical image as a node and includes a medical image hierarchy to which a node of the medical image belongs and at least one of an upper hierarchy higher than the medical image hierarchy or a lower hierarchy lower than the medical image hierarchy. The annotation support apparatus includes: an image acquisition unit that acquires the medical image; a display unit; an annotation input receiving unit that receives designation of any one of the node of the medical image or a node associated with the node of the medical image in the hierarchical structure and an input of annotation information (Continued)

related to the designated node; and an annotation storage unit that stores the annotation information to be associated with the designated node.

6 Claims, 12 Drawing Sheets

(51) Int. Cl.
*G16H 30/20* (2018.01)
*G16H 50/20* (2018.01)

(58) Field of Classification Search
USPC .............................................................. 705/2
See application file for complete search history.

(56) References Cited

U.S. PATENT DOCUMENTS

| | | | |
|---|---|---|---|
| 2013/0290826 | A1 | 10/2013 | Niwa et al. |
| 2017/0358075 | A1 | 12/2017 | Cao et al. |
| 2018/0060535 | A1* | 3/2018 | Reicher ................. G16H 50/30 |
| 2019/0251471 | A1 | 8/2019 | Morita et al. |

FOREIGN PATENT DOCUMENTS

| | | |
|---|---|---|
| JP | 2017118913 | 7/2017 |
| JP | 2017224184 | 12/2017 |
| JP | 2018014058 | 1/2018 |
| KR | 102119136 B1 * | 6/2020 |
| WO | 2017057180 | 4/2017 |
| WO | 2018042272 | 3/2018 |

OTHER PUBLICATIONS

"Office Action of Japan Counterpart Application" with English translation thereof, issued on Aug. 2, 2022, p. 1-p. 6.
Office Action of Japan Counterpart Application, with English translation thereof, issued on Jan. 17, 2023, pp. 1-5.
Iviva Dimitrovski et al., "Hierarchical annotation of medical images," Pattern Recognition, vol. 44, Mar. 2011, pp. 2436-2449.
A. Mueen et al., "Automatic Multilevel Medical Image Annotation and Retrieval," Journal of Digital Imaging, vol. 21, Sep. 2008, pp. 290-295.
Aurelia Bustos et al., "PadChest: A large chest x-ray image dataset with multi-label annotated reports," arXiv: 1901.07441v2 [eess.IV] , Feb. 2019, pp. 1-35.
"Search Report of Europe Counterpart Application", issued on Feb. 17, 2022, p. 1-p. 12.
Ryuji Hamamoto et al., "Application of artificial intelligence for cancer research; integrated analysis of cancer omics data using machine learning and deep learning," 77th Japanese Cancer Association Academic Meeting, Sep. 27, 2018, pp. 1-3.
"International Search Report (Form PCT/ISA/210) of PCT/JP2020/002603," mailed on Apr. 14, 2020, with English translation thereof, pp. 1-4.
"Written Opinion of the International Searching Authority (Form PCT/ISA/237)" of PCT/JP2020/002603, mailed on Apr. 14, 2020, with English translation thereof, pp. 1-10.
"Office Action of China Counterpart Application", issued on Dec. 4, 2023, with English translation thereof, pp. 1-24.
Office Action of China Counterpart Application, with English translation thereof, issued on Mar. 15, 2024, pp. 1-27.

\* cited by examiner

FIG. 7

ANNOTATION SUPPORT APPARATUS, ANNOTATION SUPPORT METHOD, AND ANNOTATION SUPPORT PROGRAM

CROSS-REFERENCE TO RELATED APPLICATIONS

This application is a continuation application of International Application No. PCT/JP2020/002603, filed on Jan. 24, 2020, which is incorporated herein by reference in its entirety. Further, this application claims priority from Japanese Patent Application No. 2019-010287, filed on Jan. 24, 2019, the disclosure of which is incorporated by reference herein.

BACKGROUND

Technical Field

The present invention relates to an annotation support apparatus, an annotation support method, and an annotation support program.

Related Art

In recent years, research has been conducted on automatic diagnosis support for medical images using machine learning. A large amount of learning data used for supervised learning is generally required in order to achieve a high-performance model. However, for that purpose, it is necessary to prepare annotations defined to be paired with medical images. Here, the annotations indicate information of the location or region of a lesion in the medical image and classification information related to the property and diagnosis of the lesion. For example, JP2013-132514A discloses a technique that acquires and stores annotations in response to the instruction operation of a user for a displayed medical image.

In the interpretation of medical images by a doctor, in a case in which a specific lesion is present in the medical image, the results of other examination on the lesion and the background information of the patient are referred to in addition to the location and region of the lesion, the nature of the lesion. In order to generate a high-quality model for diagnosis support, it is desirable to supply learning data which is appropriately constructed to reflect the hierarchy and relationship of annotation information as much as possible so as to reproduce the reference process of information by the doctor. In addition, in many cases, annotations have been acquired by the instruction operation of the user. However, since the labor required for this manual process is large, it is necessary to incorporate an appropriate model to save labor.

SUMMARY

Therefore, an object of the invention is to provide an annotation support apparatus, an annotation support method, and an annotation support program that can give annotation information having a hierarchy and a relationship to a medical image.

According to an aspect of the invention, there is provided an annotation support apparatus that supports generation of annotation information related to a medical image. The medical image is managed on the basis of an attribute of each medical image by a hierarchical structure that has one medical image as a node and includes at least one of a medical image hierarchy to which the node of the medical image belongs, an upper hierarchy higher than the medical image hierarchy, or a lower hierarchy lower than the medical image hierarchy. The annotation support apparatus comprises: an image acquisition unit that acquires the medical image; a display unit that displays the medical image; an annotation input receiving unit that receives designation of any one of the node of the medical image or a node associated with the node of the medical image in the hierarchical structure and an input of annotation information which is information related to the designated node; and an annotation storage unit that stores the annotation information to be associated with the designated node.

According to another aspect of the invention, there is provided an annotation support method performed in an annotation support apparatus that supports generation of annotation information related to a medical image. The medical image is managed on the basis of an attribute of each medical image by a hierarchical structure that has one medical image as a node and includes at least one of a medical image hierarchy to which the node of the medical image belongs, an upper hierarchy higher than the medical image hierarchy, or a lower hierarchy lower than the medical image hierarchy. The annotation support method comprises: an image acquisition step of acquiring the medical image; a display step of displaying the medical image; an annotation input receiving step of receiving designation of any one of the node of the medical image or a node associated with the node of the medical image in the hierarchical structure and an input of annotation information which is information related to the designated node; and an annotation storage step of storing the annotation information to be associated with the designated node.

According to yet another aspect of the invention, there is provided an annotation support program that causes a computer to function as an annotation support apparatus supporting generation of annotation information related to a medical image. The medical image is managed on the basis of an attribute of each medical image by a hierarchical structure that has one medical image as a node and includes at least one of a medical image hierarchy to which the node of the medical image belongs, an upper hierarchy higher than the medical image hierarchy, or a lower hierarchy lower than the medical image hierarchy. The annotation support program causes the computer to implement: an image acquisition function of acquiring the medical image; a display function of displaying the medical image; an annotation input receiving function of receiving designation of any one of the node of the medical image or a node associated with the node of the medical image in the hierarchical structure and an input of annotation information which is information related to the designated node; and an annotation storage function of storing the annotation information to be associated with the designated node.

According to the above-described aspects, the medical image is managed by the hierarchical structure including the medical image hierarchy to which the node of the medical image belongs and at least one of the upper hierarchy higher than the medical image hierarchy or the lower hierarchy lower than the medical image hierarchy. Then, the annotation information is received together with the designation of any one of the node of the displayed medical image or any node associated with the node, and the received annotation information is stored so as to be associated with the designated node. Therefore, a data group of the hierarchical structure in which annotation information is appropriately associated with the node of the medical image and a node associated with the node is obtained. Learning data is extracted from the data group to generate a model for achieving an automatic diagnosis in which the reference process of various kinds of information by the doctor is reflected.

According to still yet another aspect, in the annotation support apparatus, the hierarchical structure may include the medical image hierarchy and at least one of the upper hierarchy or the lower hierarchy.

According to the above-described aspect, it is possible to appropriately associate the information of the upper hierarchy, such as patient information, and the information of the lower hierarchy, such as finding information, with the information of the medical image.

According to yet still another aspect, the annotation support apparatus may further comprise a region designation receiving unit that receives designation of a finding region which is a portion of the medical image displayed by the display unit and is a region having a finding attached thereto. The hierarchical structure may include the medical image hierarchy and the lower hierarchy. The annotation input receiving unit may receive an input of annotation information for the finding region. The annotation storage unit may store finding information indicating the finding region as a node associated with the medical image in the hierarchy lower than the medical image hierarchy and store the input annotation information to be associated with the node.

According to the above-described aspect, the input of the annotation information for the finding region designated as a portion of the medical image is received, and the finding information and the annotation information are stored as nodes in the hierarchy lower than the medical image. Therefore, the medical image, the finding information, and the annotation information for the finding are managed while having an appropriate hierarchical relationship therebetween.

According to still yet another aspect, in the annotation support apparatus, the region designation receiving unit may receive designation of a region having any shape in the medical image as the designation of the finding region.

According to the above-described aspect, the designation of the finding region having any shape is received. Since the designation of the finding region is not limited to the designation by, for example, a specific marker, it is possible to obtain the finding information in which a lesion region is appropriately designated.

According to yet still another aspect, in the annotation support apparatus, the annotation input receiving unit may receive the input of the annotation information for the finding region, on the basis of reception of an operation of dragging and dropping an object indicating the annotation information to the finding region in the medical image displayed by the display unit.

According to the above-described aspect, it is possible to easily associate the annotation information with the finding region.

According to still yet another aspect, in the annotation support apparatus, the hierarchical structure may include patient information that identifies a patient as a node in the upper hierarchy. The annotation input receiving unit may receive an input of annotation information for the patient information indicating the patient which is associated with the medical image. The annotation storage unit may store the input annotation information to be associated with the node of the patient information.

According to the above-described aspect, the patient information for identifying the patient corresponding to the medical image is managed as a node in the hierarchy higher than the medical image by the hierarchical structure, and the annotation information related to the patient is stored so as to be associated with the patient information. Therefore, the medical image, the patient information, and the annotation information related to the patient are managed while having an appropriate hierarchical relationship therebetween.

According to yet still another aspect, in the annotation support apparatus, the annotation information may include relationship information indicating a relationship with a node other than the node associated with the annotation information.

According to the above-described aspect, each node can include, for example, the association between the medical images and the association between the finding information items as the annotation information items. Therefore, in a case in which the information associated with a certain node has a relationship with the information associated with another node, an information group including the relationship information is used for training a model for automatic diagnosis, which makes it possible to perform automatic diagnosis in which the relationship has been reflected.

According to still yet another aspect, the annotation support apparatus may further comprise: a learning data acquisition unit that acquires, as a learning data set, a data set including at least one medical image and annotation information associated with a node of the one medical image in information managed by the hierarchical structure; a model generation unit that generates an annotation guide model, which receives a medical image as an input and outputs annotation information related to the medical image, with machine learning using the learning data set acquired by the learning data acquisition unit; and an annotation guide unit that displays an output obtained by inputting the medical image, which is acquired by the image acquisition unit and is to be annotated, to the annotation guide model to be associated with the medical image to be annotated.

According to the above-described aspect, the annotation guide model is generated by the machine learning using the learning data set extracted from the information group managed by the hierarchical structure. A medical image is input to the generated annotation guide model, and candidates of the annotation information to be associated with the medical image are output. Then, the candidates of the annotation information are displayed so as to be associated with the medical image and are presented to the user. Therefore, it is possible to promote the annotation work of the user.

According to yet still another aspect, in the annotation support apparatus, the learning data acquisition unit may acquire, as the learning data set, a data set including at least one medical image and annotation information associated with at least one of a node of the one medical image or another node associated with the node of the one medical image in the information managed by the hierarchical structure.

According to the above-described aspect, in a case in which the hierarchical structure managing the medical images consists of a plurality of hierarchies, it is possible to acquire a learning data set that appropriately includes necessary information according to the setting of a learning task in model generation.

According to still yet another aspect of the invention, there is provided an annotation support apparatus that supports generation of annotation information related to a medical image. The medical image associated with annotation information in advance is capable of being acquired.

The annotation support apparatus comprises: a learning data acquisition unit that acquires, as a learning data set, a data set including the medical image and the annotation information associated with the medical image; a model generation unit that generates an annotation guide model, which receives a medical image as an input and outputs annotation information related to the medical image, with machine learning using the learning data set acquired by the learning data acquisition unit; an image acquisition unit that acquires the medical image to be annotated; a display unit that displays the medical image acquired by the image acquisition unit; an annotation guide unit that displays an output obtained by inputting the medical image acquired by the image acquisition unit to the annotation guide model to be associated with the medical image to be annotated which is displayed by the display unit; an annotation input receiving unit that receives an input of annotation information related to the medical image to be annotated; and an annotation storage unit that stores the annotation information received by the annotation input receiving unit to be associated with the medical image to be annotated.

According to one aspect of the invention, it is possible to add annotation information having a hierarchy and a relationship to a medical image.

BRIEF DESCRIPTION OF THE DRAWINGS

FIG. 7 is a diagram illustrating an example of the input of annotation information for the medical image.

DESCRIPTION OF EMBODIMENTS

Figure 1:
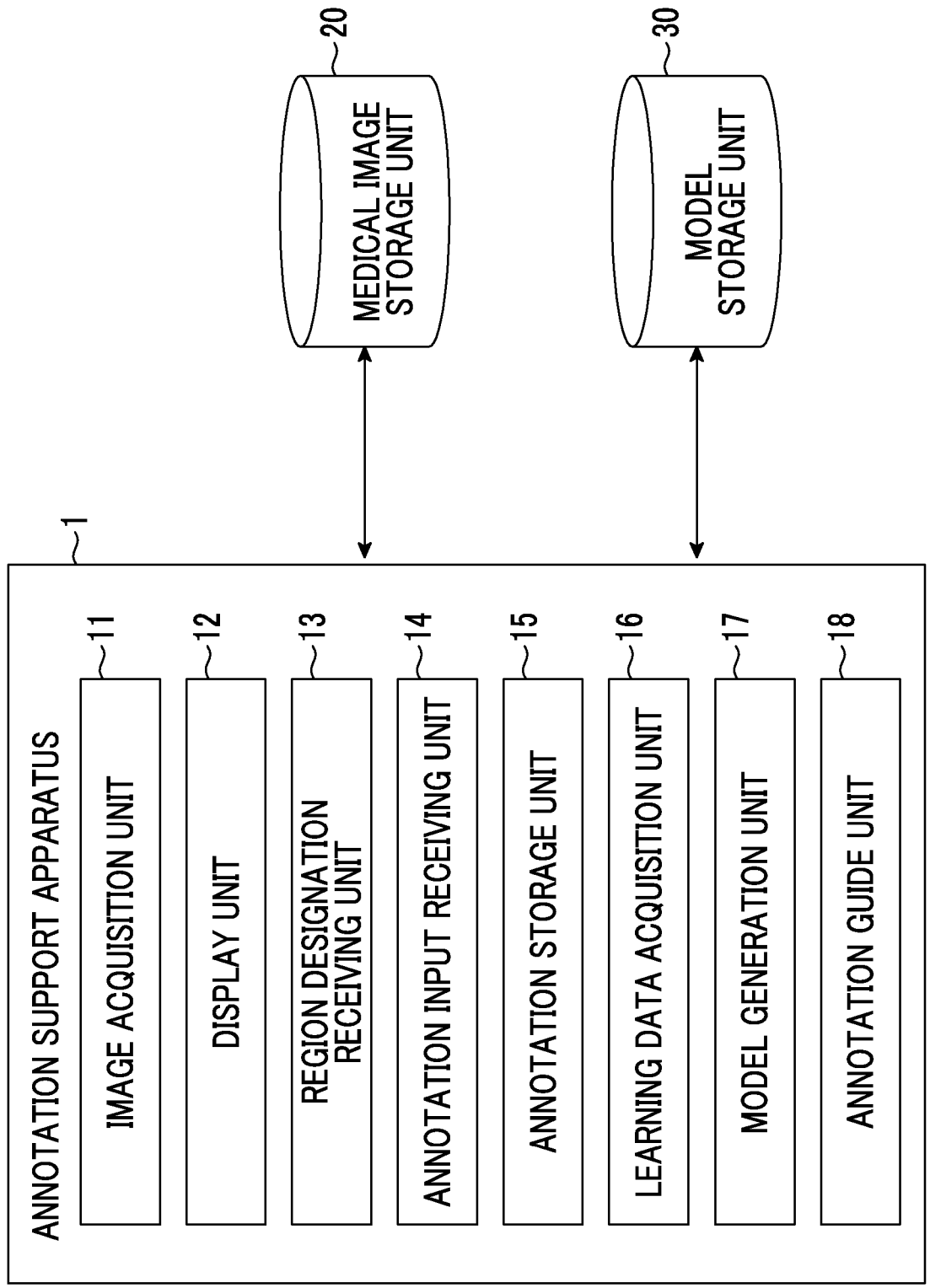
FIG. 1 is a block diagram illustrating a functional configuration of an annotation support apparatus according to an embodiment.

Hereinafter, an embodiment of the invention will be described in detail with reference to the accompanying drawings. In addition, in the description of the drawings, the same or equivalent elements are denoted by the same reference numerals, and duplicate description will be omitted.

FIG. 1 is a diagram illustrating a functional configuration of an annotation support apparatus according to this embodiment. An annotation support apparatus 1 is a device that supports the generation of annotation information related to medical images.

As illustrated in FIG. 1, the annotation support apparatus 1 comprises an image acquisition unit 11, a display unit 12, a region designation receiving unit 13, an annotation input receiving unit 14, an annotation storage unit 15, a learning data acquisition unit 16, a model generation unit 17, and an annotation guide unit 18. Each functional unit included in the annotation support apparatus 1 according to this embodiment may be distributed and configured in a plurality of devices. In addition, each functional unit included in the annotation support apparatus 1 is implemented by hardware or software, or any combination thereof.

As illustrated in FIG. 1, the annotation support apparatus 1 can access storage units such as a medical image storage unit 20 and a model storage unit 30. The storage units 20 and 30 are configured to be accessible by the annotation support apparatus 1 through a network or a predetermined communication unit. Further, the storage units 20 and 30 may be provided in the annotation support apparatus 1.

Before each functional unit of the annotation support apparatus 1 is described, the storage units 20 and 30 will be described. The medical image storage unit 20 is a storage unit that stores the medical images acquired in various examinations performed on patients.

The medical image is, for example, a DICOM image which is one of the standard formats of the medical images. Examples of the medical image may include images indicating the results of various examinations such as an X-ray examination, a CT examination, an MRI examination, a PET examination, an ultrasound examination, and an endoscopic examination. Further, the medical images may include the information of, for example, a JPEG image, a BMP image, a PNG image, and an MP4 moving image as photographs and moving images recorded in the process of a medical treatment, in addition to these images. In addition, the medical image storage unit 20 manages the medical images using a hierarchical structure on the basis of the attributes of each medical image, which will be described in detail below.

The model storage unit 30 is a storage unit that stores an annotation guide model which will be described in detail below. The annotation guide model is a model that is generated by machine learning, receives a medical image as an input, and outputs annotation information related to the medical image.

Figure 2:
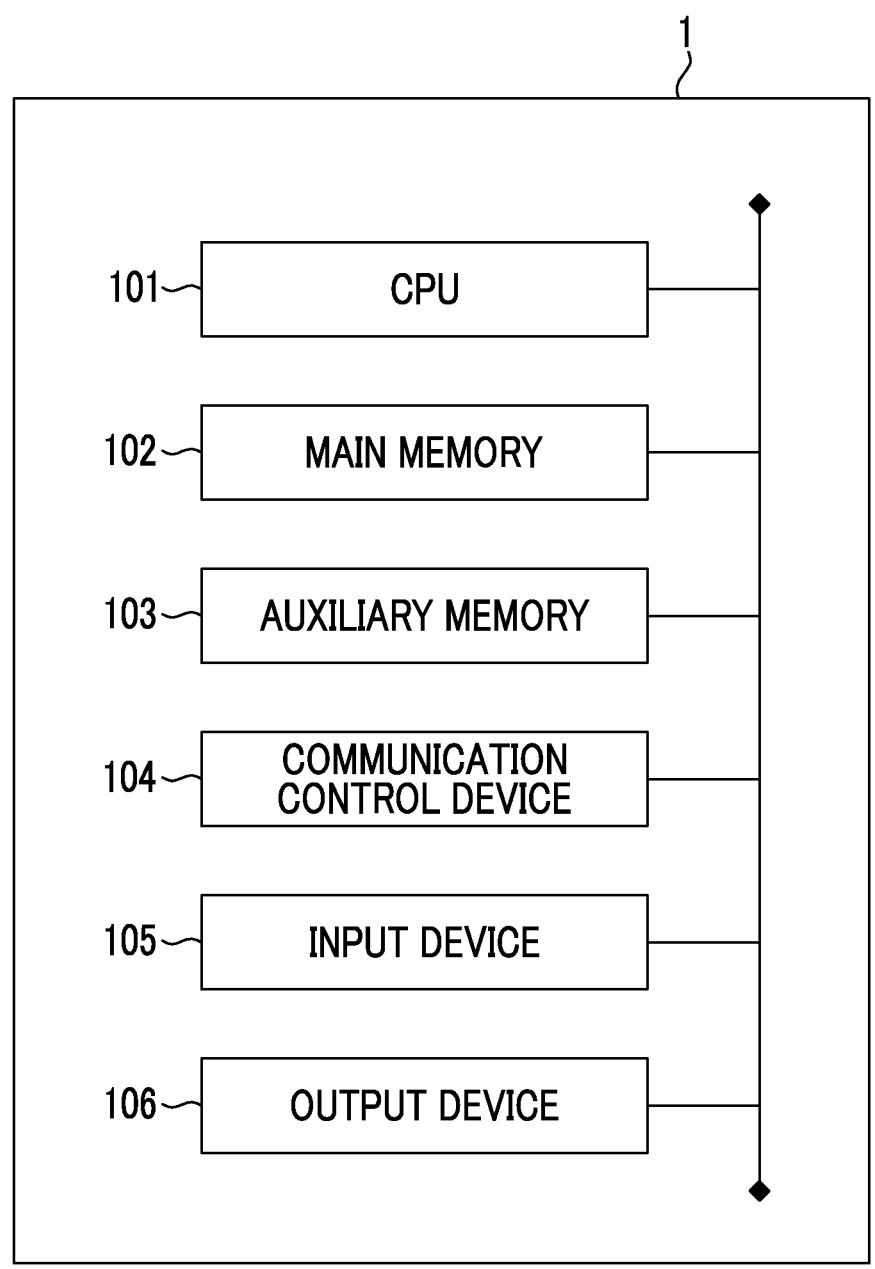
FIG. 2 is a diagram illustrating a hardware configuration of the annotation support apparatus.

FIG. 2 is a diagram illustrating a hardware configuration of the annotation support apparatus 1. Physically, as illustrated in FIG. 2, the annotation support apparatus 1 is configured as a computer system that includes, for example, a CPU 101, a main memory 102 composed of memories, such as a RAM and a ROM, an auxiliary memory 103 composed of a hard disk, a memory, and the like, and a communication control device 104. The annotation support apparatus 1 may further include an input device 105, such as a keyboard, a touch panel, or a mouse, which is an input device and an output device 106 such as a display. In addition, the annotation support apparatus 1 may be configured to include a GPU.

Each function illustrated in FIG. 1 is implemented by reading predetermined computer software to hardware, such as the CPU 101 and the main memory 102 illustrated in FIG.

2, operating the communication control device 104 and the like under the control of the CPU 101, and performing the reading and writing of data from and to the main memory 102 or the auxiliary memory 103. Data or a database required for processing is stored in the main memory 102 and the auxiliary memory 103.

The functional units of the annotation support apparatus 1 will be described again with reference to FIG. 1. The image acquisition unit 11 acquires medical images. Specifically, the image acquisition unit 11 acquires the medical images stored in the medical image storage unit 20.

The medical images are images acquired in various examinations performed on the patients as described above. The medical image can have, as attribute information, patient information for identifying the patient, the type of examination, and other information. For example, in a case in which a plurality of images are acquired in one examination, information for grouping the plurality of images may be included as the attribute information.

The medical image storage unit 20 manages the medical images using the hierarchical structure on the basis of the attributes of each medical image. Specifically, the hierarchical structure related to the medical images has the medical image as a node and includes at least one of a medical image hierarchy to which the node of the medical image belongs, an upper hierarchy which is higher than the medical image hierarchy, or a lower hierarchy which is lower than the medical image hierarchy. The upper hierarchy can include, for example, patient information as a node. The lower hierarchy can include, for example, finding information attached to the medical image as a node.

In addition, the hierarchical structure in which the medical images are managed may include the medical image hierarchy and at least one of the upper hierarchy or the lower hierarchy. The management of the medical images by the hierarchical structure makes it possible to appropriately associate the information of the upper hierarchy, such as patient information, and the information of the lower hierarchy, such as finding information, with the information of the medical images.

Figure 3:
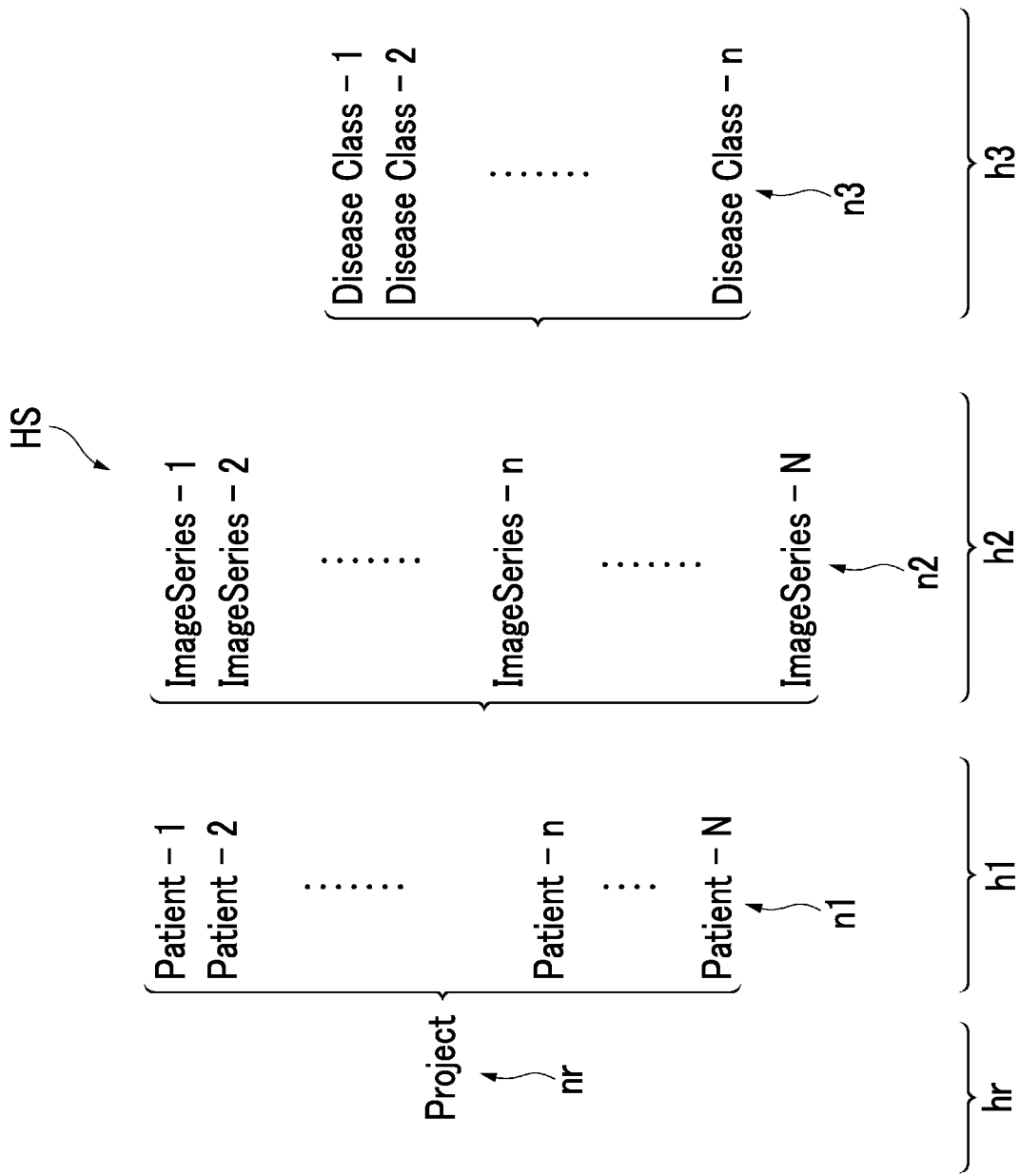
FIG. 3 is a diagram illustrating a hierarchical structure in which medical images are managed, patient information is included in a hierarchy higher than the medical images, and finding information is included in a hierarchy lower than the medical images.

FIG. 3 is a diagram schematically illustrating an example of a hierarchical structure HS in which medical images are managed. In the example illustrated in FIG. 3, the hierarchical structure HS includes a medical image hierarchy, an upper hierarchy which is higher than the medical image hierarchy, and a lower hierarchy which is lower than the medical image hierarchy. As illustrated in FIG. 3, the hierarchical structure HS includes a root hierarchy hr, a first hierarchy h1, a second hierarchy h2, and a third hierarchy h3.

The hierarchical structure HS illustrated in FIG. 3 has a project nr represented by "Project" as a root and manages various kinds of information in the lower hierarchies. In the example illustrated in FIG. 3, a case in which the project nr is provided as a root node is described. However, the hierarchical structure may be configured without having the project as the root node.

A medical image n2 which is represented by "Image-Series" constitutes a node belonging to the second hierarchy h2. The medical image has an aspect as examination information of each examination acquired in each examination among various examinations performed on a certain a patient.

The first hierarchy h1 which is higher than the node of the medical image n2 has patient information n1 represented by "Patient" as a node. In the patient information n1, a plurality of medical images related to the same patient are grouped on the basis of the patient information that each medical image n2 has as the attribute information.

The third hierarchy h3 which is lower than the node of the medical image n2 has finding information n3 represented by "Disease Class" as a node. The finding information n3 is information that is defined to have regionality for a portion of the medical image. As illustrated in FIG. 3, a plurality of finding information items can be defined for one medical image.

Figure 4:
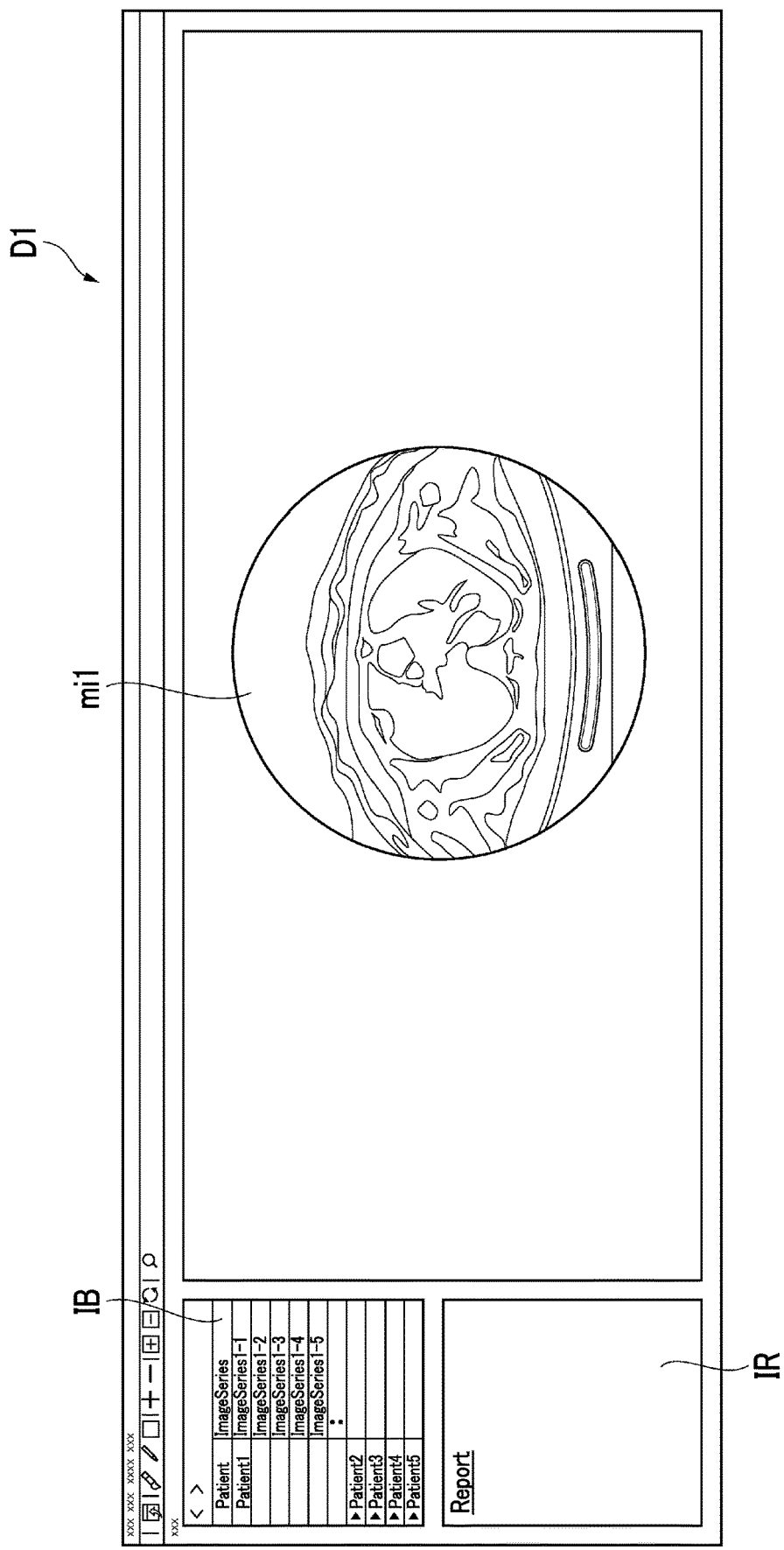
FIG. 4 is a diagram illustrating an example of the medical image displayed on a display device.

Referring to FIG. 1 again, the display unit 12 displays the medical image. Specifically, the display unit 12 displays the medical image acquired by the image acquisition unit 11 on the display. FIG. 4 is a diagram illustrating an example of the medical image displayed on the display by the display unit 12. As illustrated in FIG. 4, a medical image mi1 as one of the examination results is displayed on a display screen D1.

In addition, the display screen D1 includes a browse list D3 and an interpretation report display portion IR. The browse list IB is a portion in which a medical image list is displayed and which is used for selecting the medical image to be displayed on the display screen D1. In a case in which the input of the user's selection for a plurality of medical images displayed in the browse list IB is acquired, the display unit 12 displays the selected medical image on the display screen D1. In addition, the list displayed in the browse list IB reflects the configuration of the hierarchical structure HS described with reference to FIG. 3. The interpretation report display portion IR is a portion that presents the data of the interpretation report stored so as to be association with the medical image displayed on the display screen D1 to the user as reference information in a case in which the user inputs an annotation. Further, any clinical information stored in a text format, such as a medical record, can be displayed in the interpretation report display portion IR so as to be associated with the displayed medical image.

Figure 5:
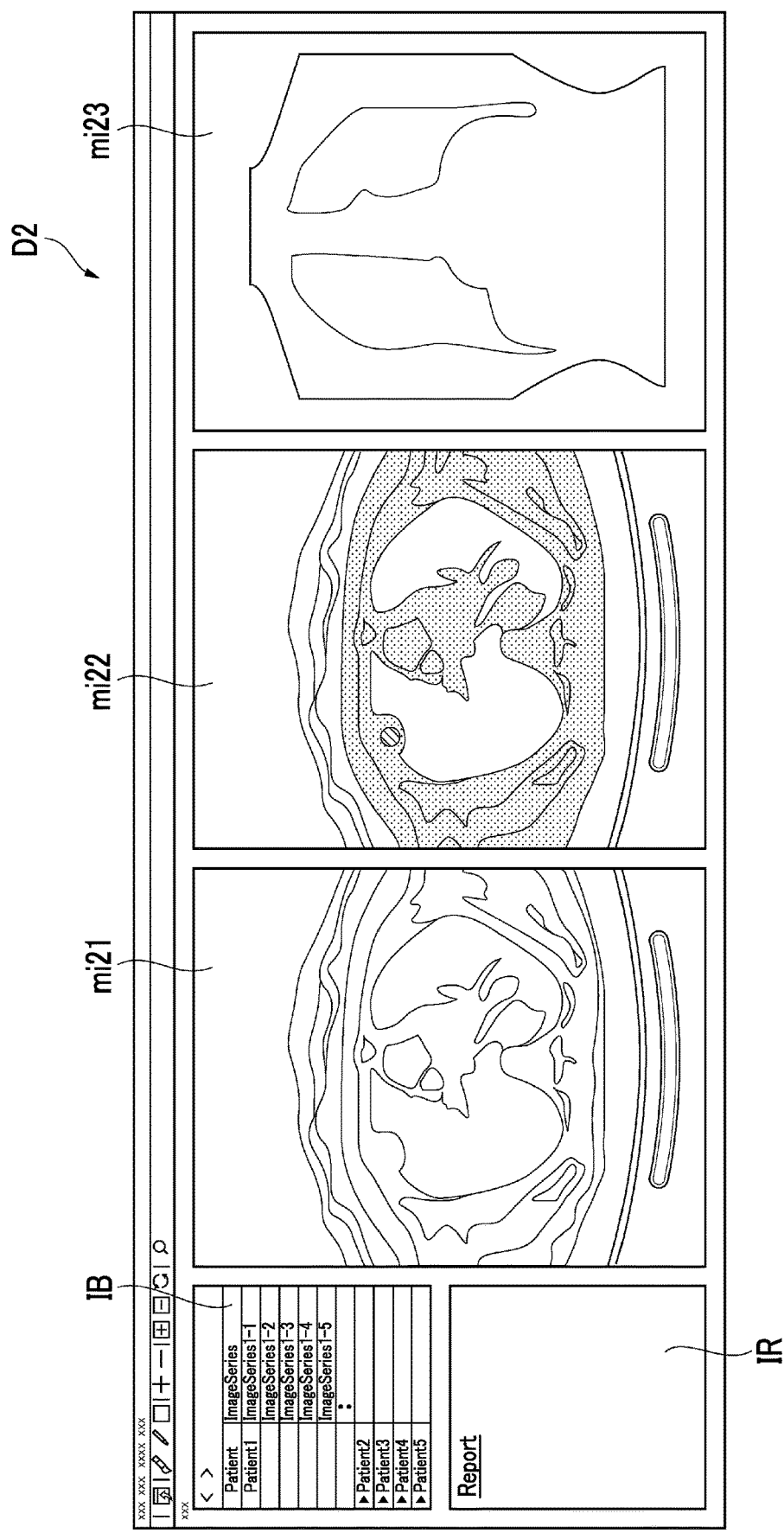
FIG. 5 is a diagram illustrating an example in which a plurality of medical images are displayed on the display device.

FIG. 5 is a diagram illustrating an example in which the display unit displays a plurality of medical images on the display. As illustrated in FIG. 5, a plurality of medical images mi21, mi22, and mi23 are displayed on a display screen D2. The medical image mi21 is a medical image obtained by a CT examination. The medical image mi22 is a medical image obtained by a PET examination. The medical image mi23 is a medical image obtained by an X-ray examination. As illustrated in FIG. 5, the annotation support apparatus 1 according to this embodiment can display medical images as the results of a plurality of related examinations side by side.

Referring to FIG. 1 again, the region designation receiving unit 13 receives the designation of a finding region on the medical image displayed by the display unit 12. The finding region is a portion of the medical image and is a region to which a finding is attached. The designation of the finding region can be received in various aspects.

For example, the region designation receiving unit 13 can receive the designation of the finding region by the input of the designation operation of the user for a portion of the displayed medical image. Specifically, for example, in a case in which the user places a pointer at any location in the medical image and performs an operation such as clicking, the region designation receiving unit 13 receives the location as the finding region.

In addition, the region designation receiving unit 13 may receive the designation of any region in the medical image as the designation of the finding region. Specifically, for example, in a case in which the user operates various pointing devices to input a figure having a shape that surrounds any region in the medical image, the region designation receiving unit 13 can receive the region having any shape as the designation of the finding region. Therefore, since the designation of the finding region is not limited to the designation using, for example, a specific marker, it is possible to obtain the finding information in which a lesion region is appropriately designated.

The annotation input receiving unit 14 receives the designation of the node of the medical image and any node associated with the node of the medical image in the hierarchical structure and the input of annotation information which is information related to the designated nodes. In this embodiment, the annotation input receiving unit 14 receives the designation of any node in the hierarchical structure HS described with reference to FIG. 3. Then, the annotation input receiving unit 14 receives the input of the information to be associated with the designated node as the input of the annotation information.

The annotation storage unit 15 stores the annotation information received by the annotation input receiving unit 14 so as to be associated with the designated node. Specifically, the annotation storage unit 15 stores the input annotation information so as to be associated with the designated node among the nodes managed in the hierarchical structure HS described with reference to FIG. 3.

Figure 6:
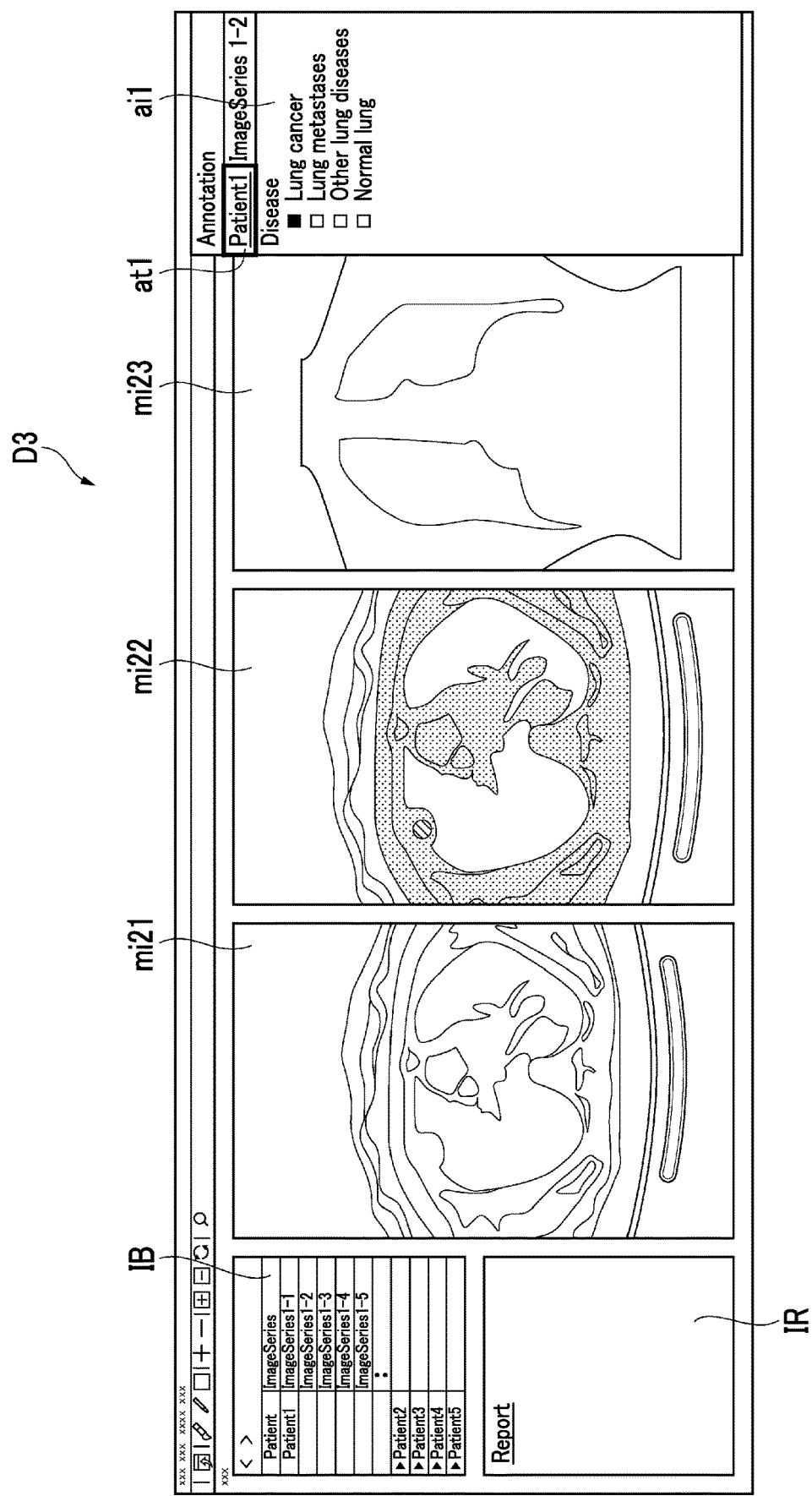
FIG. 6 is a diagram illustrating an example of the input of annotation information for patient information.

Hereinafter, a specific example of the reception of the annotation information will be described with reference to FIGS. 6 to 8. FIG. 6 is a diagram illustrating an example of the input of the annotation information for patient information. As illustrated in FIG. 6, the display unit 12 displays a plurality of medical images mi21, mi22, and mi23 on a display screen D3.

The medical images mi21, mi22, and mi23 are medical images indicating the examination results of the patient identified by "Patient1". Each of the medical images mi21, mi22, and mi23 constitutes each node belonging to the second hierarchy h2 in the hierarchical structure HS. The nodes of the medical images are associated with the node of the patient information "Patient1" in the first hierarchy h1.

For example, in a case in which the designation of a tab at1 on the display screen D3 is input, the annotation input receiving unit 14 receives the input as the designation of the node of the patient information "Patient1".

Further, in a case in which annotation information is input to an annotation information input field ai1, the annotation input receiving unit 14 receives the input as the annotation information to be associated with the node of the patient information "Patient1". Examples of the annotation information to be managed for each patient include the type of the main disease of the patient and the sex of the patient. In the example illustrated in FIG. 6, information "Diseases: Lung cancer" is input as the annotation information to be associated with the patient information "Patient1".

The annotation storage unit 15 stores the input annotation information "Diseases: Lung cancer" so as to be associated with the node of the patient information "Patient1".

According to the example described with reference to FIG. 6, the patient information for identifying the patient related to the medical image is managed as the node in the hierarchy higher than the medical image in the hierarchical structure, and the annotation information related to the patient is stored so as to be associated with the patient information. Therefore, the medical image, the patient information, and the annotation information related to the patient are managed while having an appropriate hierarchical relationship therebetween.

Figure 7:
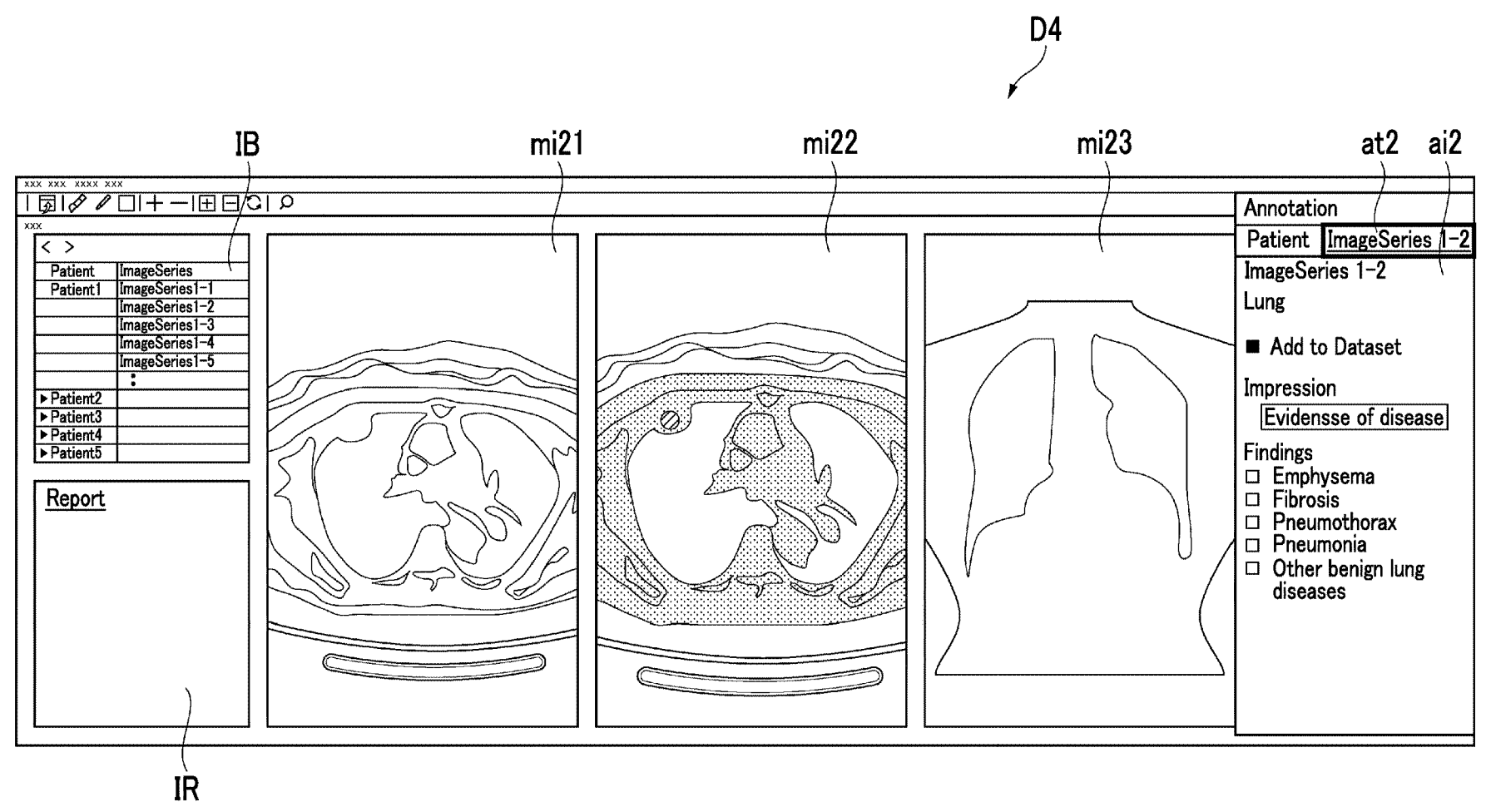

FIG. 7 is a diagram illustrating an example of the input of annotation information for a medical image. As illustrated in FIG. 7, the display unit 12 displays a plurality of medical images mi21, mi22, and mi23 on a display screen D4.

The medical images mi21, mi22, and mi23 are medical images indicating the examination results of the patient identified by "Patient1". Each of the medical images mi21, mi22, and mi23 constitutes each node belonging to the second hierarchy h2 in the hierarchical structure HS. The nodes of the medical images are associated with the node of the patient information "Patient1" in the first hierarchy h1.

For example, in a case in which the designation of a tab at2 on the display screen D4 is input, the annotation input receiving unit 14 receives the input of the designation as the designation of the node of a medical image "Image Series 1-2".

Further, in a case in which annotation information is input to an annotation information input field ai2, the annotation input receiving unit 14 receives the input as the annotation information to be associated with the node of the medical image "Image Series 1-2".

The annotation information to be managed for each medical image is information to be managed for each examination related to the acquisition of the image. Examples of the annotation information include a clinical situation, such as "before surgery" or "after surgery", and finding information to be defined on the basis of the information of the entire image (for example, tumor staging or the like). Further, the relationship between the medical images may be defined as the annotation information of the medical images. For the relationship of one medical image with another medical image, another medical image may be explicitly designated as the annotation information of one medical image to define the content of the relationship. In addition, the relationship may be implicitly defined on the basis of the association with the node of the same patient information.

The annotation storage unit 15 stores the annotation information input in the annotation information input field ai2 so as to be associated with the node of the medical image "Image Series 1-2".

Figure 8:
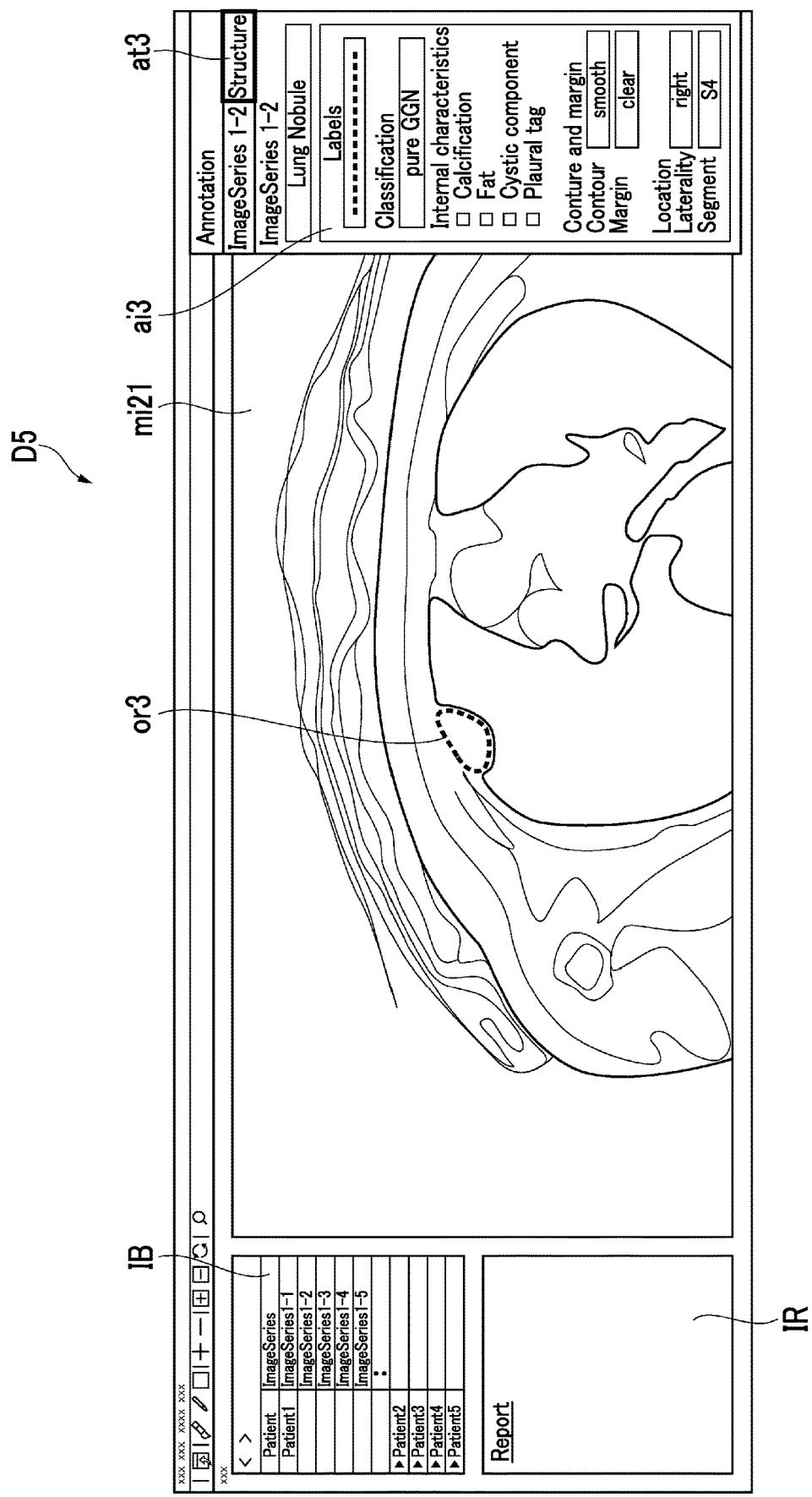
FIG. 8 is a diagram illustrating an example of the designation of a region related to a finding in the medical image and the input of annotation information for the finding information.

FIG. 8 is a diagram illustrating an example of the designation of a region related to a finding in the medical image and the input of annotation information for the finding information. As illustrated in FIG. 8, the display unit 12 displays the medical image mi21 on a display screen D5.

The medical image mi21 is a medical image indicating the examination result of the patient identified by "Patient1". The medical image mi21 constitutes a node belonging to the second hierarchy h2 in the hierarchical structure HS, and the node is associated with the node of the patient information "Patient1" in the first hierarchy h1.

For example, the region designation receiving unit 13 receives the designation of a finding region or3 on the basis of the input of the designation of the region by the user in a state in which the medical image "Image Series 1-2" is selected by the designation of a tab on the display screen D5. The finding region is a portion of the medical image and is used for defining a region such as a lesion.

As illustrated in FIG. 8, the region designation receiving unit 13 can receive the designation of a region having any shape in the medical image as the designation of the finding region. As such, since the designation of the finding region is not limited to the designation by a specific marker or the like, it is possible to obtain the finding information in which a lesion region is appropriately designated.

In addition, in a case in which annotation information is input to an annotation information input field ai3 in a state in which a tab at3 associated with the finding region or3 is designated, the annotation input receiving unit 14 receives the input as the annotation information to be associated with the finding region or3. The annotation information for each finding is information that is defined to have regionality for a predetermined region of the image and is, for example, information indicating image characteristics that are expressed in words by a clinician. In this embodiment, the annotation information is input by labeling the finding region with qualitative information indicated by the finding region.

The annotation storage unit 15 stores the finding information indicating the finding region as a node associated with the medical image in the hierarchy lower than the hierarchy of the medical image and stores the input annotation information so as to be associated with the node. Specifically, the annotation storage unit 15 stores the finding information indicating the finding region or3 as a node associated with the medical image "Image Series 1-2" in the third hierarchy h3 which is lower than the second hierarchy h2 in the hierarchical structure HS. Further, the annotation storage unit 15 stores the annotation information input to the annotation information input field ai3 so as to be associated with the node of the finding information indicating the finding region or3.

For example, in a case in which there are a plurality of lesions in one medical image, the region designation receiving unit 13 can receive the designation of a plurality of finding regions in the one medical image. For example, the designation of a plurality of finding regions may be received by receiving labeling with a plurality of different colors or line types on the display screen. In this case, the annotation input receiving unit 14 receives the input of annotation information for each finding region. Then, the annotation storage unit 15 generates a node corresponding to each finding region as a node in a hierarchy that is lower than the node of one medical image and stores the input annotation information so as to be associated with each node.

In addition, the annotation information can be input in various aspects. For example, an object indicating the annotation information input to the annotation information input field ai3 may be displayed in, for example, the annotation information input field ai3, and the annotation storage unit 15 may associate the input annotation information with the node of the finding region on the basis of the reception of an operation of dragging-and-dropping the object to the finding region. This makes it possible to easily associate the annotation information with the finding region.

Further, the relationship between the findings in the image may be defined as the annotation information of the finding information. For the relationship of one finding information item with another finding information item, another finding information item may be explicitly designated as the annotation information of the one finding information item to define the content of the relationship. In addition, the relationship may be implicitly defined on the basis of the association with the hierarchy lower than the node of the same medical image.

Figure 9:
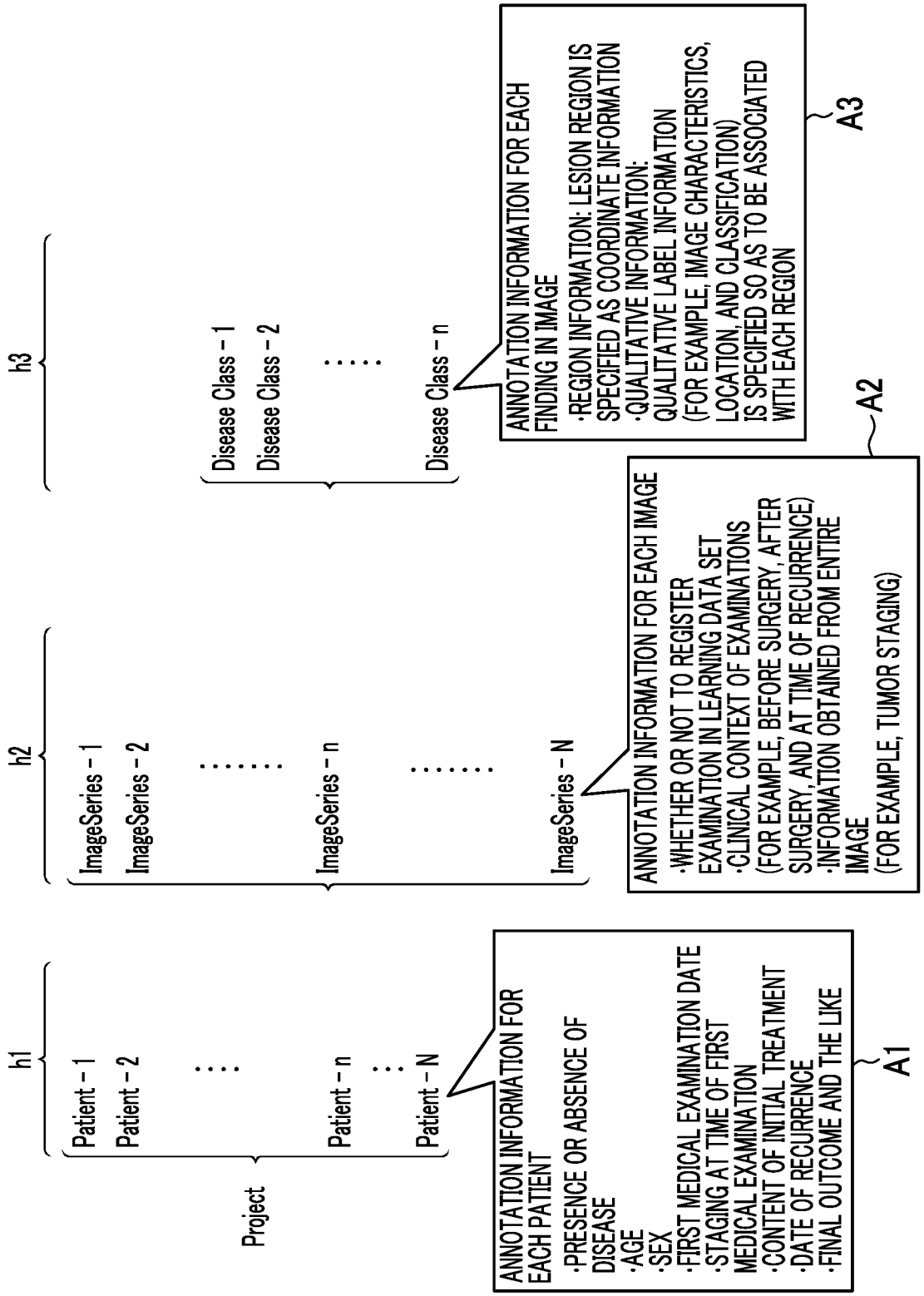
FIG. 9 is a diagram illustrating an example of annotation information associated with each information item of each hierarchy managed in the hierarchical structure.

FIG. 9 is a diagram illustrating an example of the annotation information associated with each information item of each hierarchy managed in the hierarchical structure. As described above, the annotation storage unit 15 stores the input annotation information so as to be associated with the node designated in a case in which the annotation information is input.

In FIG. 9, annotation information A1 is annotation information for each patient associated with the node of the patient information represented by "Patient" which belongs to the first hierarchy h1. The annotation information A1 can include, for example, information, such as the presence or absence of a disease, age, sex, the date of the first medical examination, staging at the time of the first medical examination, the content of an initial treatment, the date of recurrence, and the final outcome.

Annotation information A2 is annotation information for each medical image (each examination) associated with the node of the medical image represented by "ImageSeries" which belongs to the second hierarchy h2. The annotation information A2 can include the clinical context (for example, before surgery, after surgery, and at the time of recurrence) of examinations and information (for example, tumor staging) obtained from the entire image. In addition, the annotation information associated with the medical image can include setting information (Add to Dataset=True/False) which is set randomly and indicates whether or not the medical image (examination) is included in a learning data set of machine learning which will be described below. The setting information can be set randomly according to the input of the user for the purpose of machine learning and the model to be generated. In a case in which "True" is input, the medical image is included in the learning data set. In addition, the predetermined setting information is not limited to be explicitly defined, and whether or not the medical image is included in the learning data set may be determined on the basis of whether or not specific annotation information is included.

Further, the node of the medical image can have information to be associated with each medical image as the annotation information. In addition, the finding information associated with the node of the medical image in the hierarchy lower than the node of the medical image can be regarded as the annotation information of the medical image. That is, the finding information can be regarded as a node in the hierarchy lower than the medical image and the annotation information of the medical image.

Annotation information A3 is annotation information for each finding associated with the node of finding information represented by "DiseaseClass" which belongs to the third hierarchy h3. The annotation information A3 can include information indicating a finding region and the qualitative information of a finding. The information indicating the finding region can include coordinate information corresponding to the format (for example, a DICOM format) of the medical image to define a lesion region. The qualitative information of the finding can include qualitative label information (for example, image characteristics, a location, and a classification) for each finding region. In addition, the node of the finding information corresponds to notation "Structure" in FIG. 8 and FIG. 10 which will be referred to below.

Referring to FIG. 1 again, the learning data acquisition unit 16 acquires, as a learning data set, a data set including at least one medical image and annotation information associated with the node of the one medical image in the information managed by the hierarchical structure. Further, in a case in which the hierarchical structure managing the medical images consists of a plurality of hierarchies, the learning data acquisition unit 16 may acquire, as the learning data set, a data set including at least one medical image and annotation information associated with at least one of the node of the one medical image or another node associated with the node of the one medical image in the information managed by the hierarchical structure. The content of the data set is determined according to a learning task in model generation which will be described below.

The model generation unit 17 generates an annotation guide model, which receives a medical image as an input and outputs annotation information related to the medical image with machine learning using the learning data set acquired by the learning data acquisition unit 16. The model generation unit 17 stores the generated annotation guide model in the model storage unit 30.

In this embodiment, the annotation guide model is generated by performing so-called supervised learning using a learning data set including a medical image as a learning target and annotation information as correct answer data associated with the learning result. The medical image included in the learning data set can be designated in, for example, the annotation information of the medical image as described above. In addition, the content of the learning task can include the classification of medical images, the detection of a specific finding, such as a lesion, included in the medical image, and the segmentation of the specific finding (the extraction of a region). However, other learning tasks may be used according to the design.

The data included in the learning data set is not limited to the annotation information of one medical image, but may include, for example, information of other nodes related to the one medical image, annotation information associated with other nodes, and information (relationship information) indicating the relationship between nodes in the same hierarchy or different hierarchies for the purpose of the model and according to the setting of tasks.

The annotation guide model is configured to include a neural network. The neural network may be configured by, for example, a convolution neural network (CNN). The annotation guide model which is a model including a trained neural network can be regarded as a program that is read or referred to by a computer, causes the computer to perform a predetermined process, and causes the computer to implement a predetermined function.

That is, the annotation guide model according to this embodiment is used in a computer comprising a CPU (or/and a GPU) and a memory. Specifically, the CPU (or/and the GPU) of the computer is operated so as to perform calculation based on, for example, a learned weighting coefficient and a response function corresponding to each layer for the input data input to an input layer of the neural network and to output results from an output layer, in response to commands from the annotation guide model stored in the memory.

The annotation guide unit 18 displays the output obtained by inputting the medical image, which is acquired by the image acquisition unit 11 and is to be annotated, to the annotation guide model so as to be associated with the medical image to be annotated.

In this embodiment, for example, the model generation unit 17 can perform machine learning, using a medical image and finding information input as annotation information for a lesion portion in the medical image as a learning data set, to generate an annotation guide model that receives the medical image as an input and outputs the finding information of the lesion portion to be associated with the medical image. Here, the finding information used for learning and the finding information output from the model include information indicating the finding region and information such as characteristics related to the finding region and the type of lesion.

Figure 10:
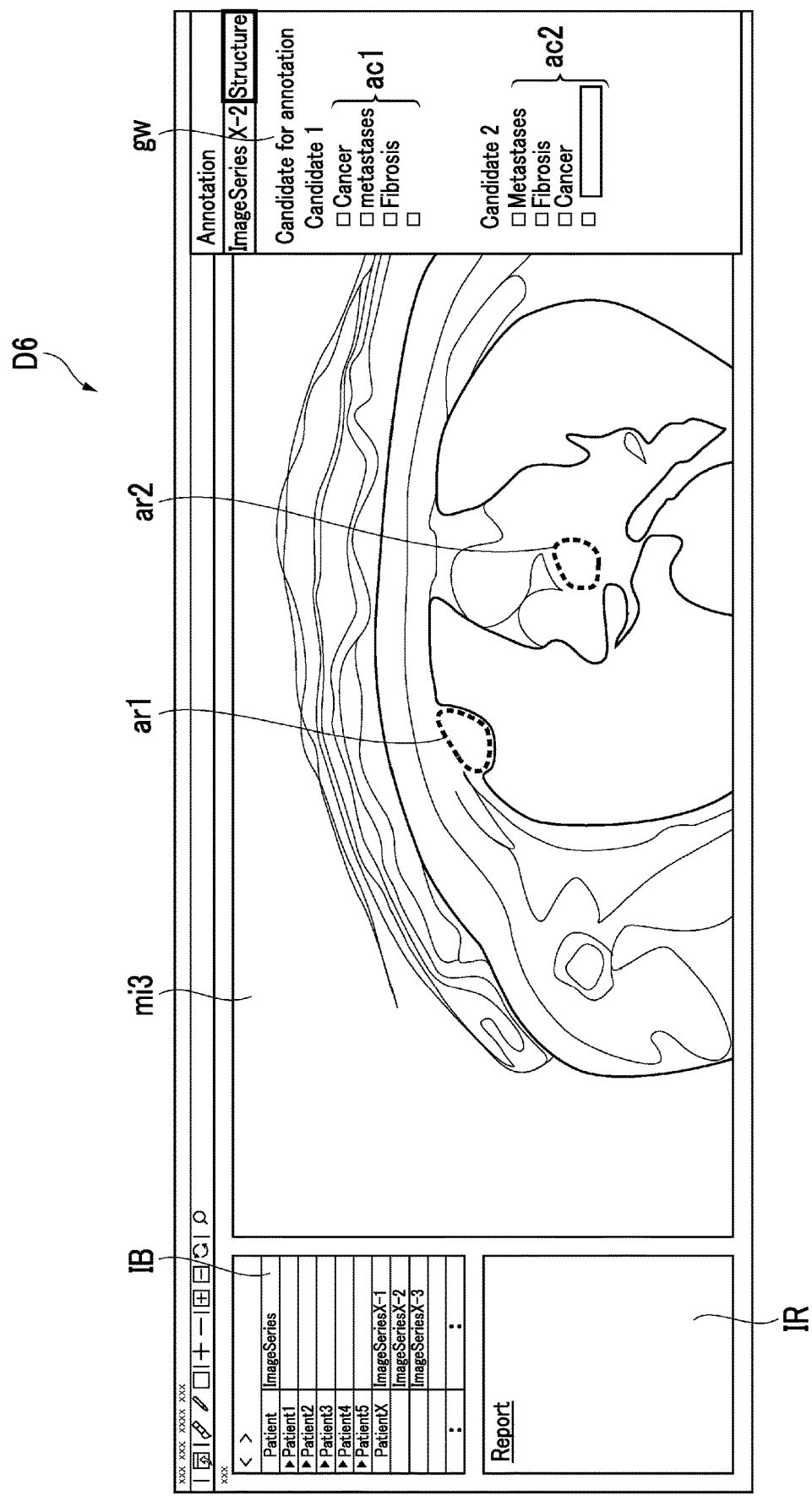
FIG. 10 is a diagram illustrating an example of the display of candidates of annotation information to be associated with a medical image.

FIG. 10 is a diagram illustrating an example of the display of candidates of annotation information to be associated with a medical image. As illustrated in FIG. 10, the display unit 12 displays a medical image mi3 to be annotated on a display screen D6.

The annotation guide unit 18 inputs the medical image mi3 to the annotation guide model and acquires the candidates of finding information as the annotation information to be associated with the medical image mi3 which has been output from the model. Specifically, as illustrated in FIG. 10, the annotation guide unit 18 acquires a finding region candidate ar1 and a finding region candidate ar2 as the candidates of the finding information which is the annotation information to be associated with the medical image mi3 and displays the candidates so as to be superimposed on the medical image mi3. Further, the annotation guide unit 18 acquires a finding information candidate ac1 to be associated with the finding region candidate ar1 and a finding information candidate ac2 to be associated with the finding region candidate ar2 and displays the finding information candidates in an annotation candidate display portion gw.

In a case in which the accumulated amount of annotation information associated with the medical image is equal to or greater than the value at which machine learning can be performed using the medical image and the annotation information as a learning data set, the model generation unit 17 can generate the annotation guide model on the basis of the accumulated medical image and annotation information. Then, the annotation guide unit 18 can acquire and output the candidates of the annotation information to be associated with the medical image to be annotated, on the basis of the generated annotation guide model. The output candidates of the annotation information are displayed so as to be associated with the medical image and are presented to the user, which makes it possible to assist the annotation work of the user and to promote the annotation work. In addition, the annotation guide model can be sequentially generated according to the accumulation of the medical image and the annotation information. Therefore, it is possible to improve the validity of the candidates of the annotation information presented to the user.

Figure 11:
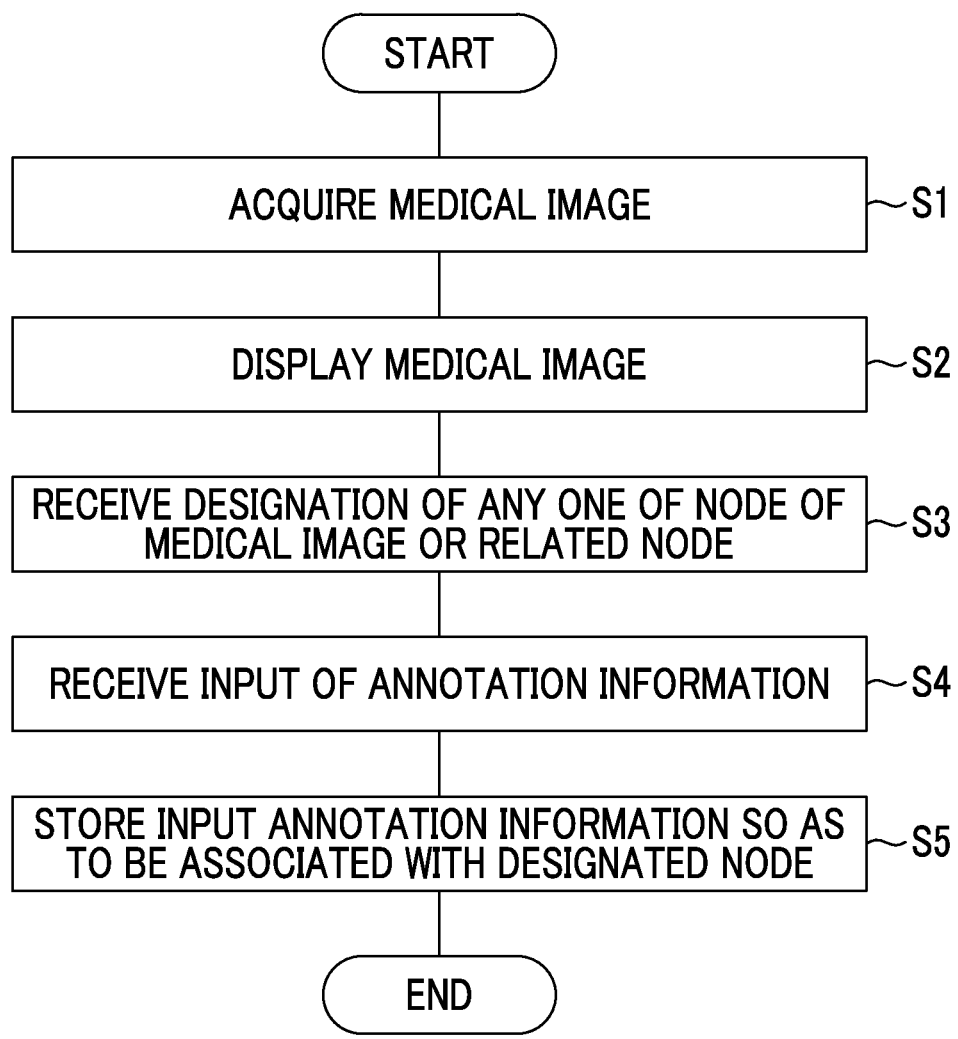
FIG. 11 is a flowchart illustrating the processing content of an annotation support method performed in the annotation support apparatus.

Next, the operation of the annotation support apparatus 1 according to this embodiment will be described with reference to FIG. 11. FIG. 11 is a flowchart illustrating the processing content of an annotation support method performed in the annotation support apparatus 1.

In Step S1, the image acquisition unit 11 acquires the medical image stored in the medical image storage unit 20. In Step S2, the display unit 12 displays the medical image acquired by the image acquisition unit 11 on a display device. In a case in which the medical image is displayed in Step S2, the annotation guide unit 18 may display the candidates of the annotation information to be associated with the displayed medical image so as to be associated with the displayed medical image.

In Step S3, the annotation input receiving unit 14 receives the designation of any one of the node of the medical image or a node associated with the node of the medical image in the hierarchical structure. Further, in Step S4, the annotation input receiving unit 14 receives the input of the annotation information to be associated with the designated node.

In Step S5, the annotation storage unit 15 stores the annotation information received by the annotation input receiving unit 14 so as to be associated with the designated node. Specifically, the annotation storage unit 15 stores the input annotation information so as to be associated with the designated node among the nodes managed in the hierarchical structure HS.

Figure 12:
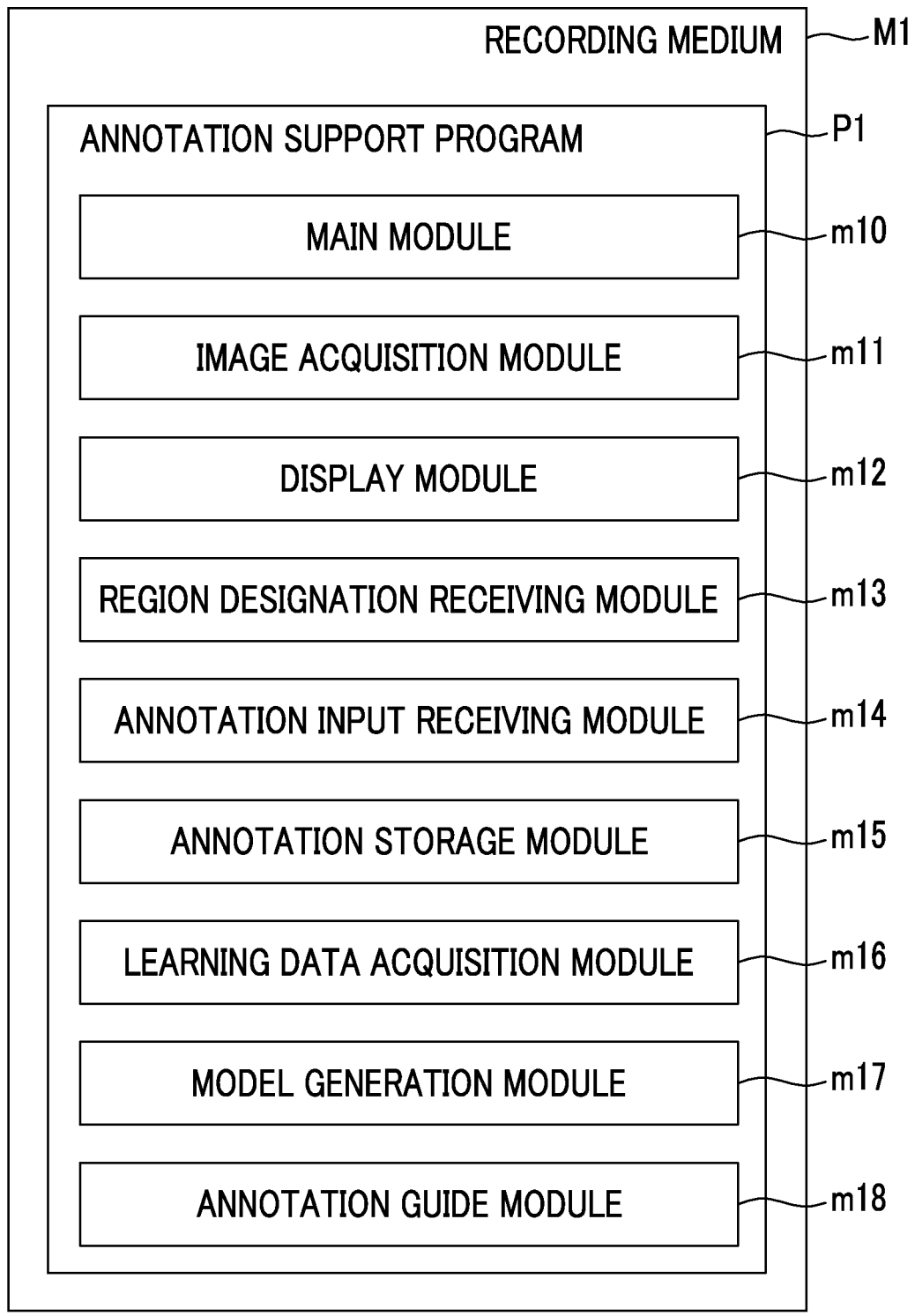
FIG. 12 is a diagram illustrating a configuration of an annotation support program.

Next, an annotation support program that causes a computer to function as the annotation support apparatus will be described with reference to FIG. 12. An annotation support program P1 illustrated in FIG. 12 includes a main module m10, an image acquisition module m11, a display module m12, a region designation receiving module m13, an annotation input receiving module m14, an annotation storage module m15, a learning data extraction module m16, a model generation module m17, and an annotation guide module m18.

The main module m10 comprehensively controls an annotation support process. The image acquisition module m11, the display module m12, the region designation receiving module m13, the annotation input receiving module m14, the annotation storage module m15, the learning data extraction module m16, the model generation module m17, and the annotation guide module m18 are executed to implement the functions of the image acquisition unit 11, the display unit 12, the region designation receiving unit 13, the annotation input receiving unit 14, the annotation storage unit 15, the learning data acquisition unit 16, the model generation unit 17, and the annotation guide unit 18 of the annotation support apparatus 1 illustrated in FIG. 1, respectively.

The annotation support program P1 may be provided by a storage medium M1 such as a magnetic disk, an optical disk, or a semiconductor memory. Further, the annotation support program P1 may be provided as a computer data signal superimposed on a carrier wave through a communication network.

In the annotation support apparatus 1, the annotation support method, and the annotation support program P1 according to this embodiment described above, the medical image is managed by the hierarchical structure including the medical image hierarchy to which the node of the medical image belongs and at least one of the upper hierarchy higher than the medical image hierarchy or the lower hierarchy lower than the medical image hierarchy. Then, the annotation information is received together with the designation of any one of the node of the displayed medical image or any node associated with the node, and the received annotation information is stored so as to be associated with the designated node. Therefore, a data group of the hierarchical structure in which annotation information is appropriately associated with the node of the medical image and a node associated with the node is obtained. Learning data is extracted from the data group to generate a model for achieving an automatic diagnosis in which the reference process of various kinds of information by the doctor is reflected.

The invention has been described in detail above on the basis of the embodiment. However, the invention is not limited to the above-described embodiment. The invention can be modified in various ways without departing from the scope and spirit thereof.

What is claimed is:

1. An annotation support apparatus that supports generation of annotation information related to a medical image, wherein the medical image is managed on the basis of an attribute of each medical image by a hierarchical structure that has one medical image as a node and includes at least one of a medical image hierarchy to which the node of the medical image belongs, an upper hierarchy higher than the medical image hierarchy, or a lower hierarchy lower than the medical image hierarchy, the annotation support apparatus comprises:
a memory;
a display unit;
at least one processor coupled to the memory and the display unit, the processor configured to:
acquire the medical image;
display the medical image;
receive designation of any one of the node of the medical image or a node associated with the node of the medical image in the hierarchical structure and an input of first annotation information which is information related to the designated node;
store the first annotation information to be associated with the designated node in the medical image hierarchy;
receive an input of second annotation information which is patient information indicating a patient associated with the medical image;
store the second annotation information to be associated with a node in the upper hierarchy;
receive designation of a finding region associated with a lesion in the medical image;
receive an input of third annotation information which is finding information indicating the finding region;
store the third annotation information to be associated with a node in the lower hierarchy;
generate an annotation guide model, which receives an input medical image and outputs output annotation information related to the input medical image, with machine learning using a learning data set comprises the medical image, the first annotation information associated with the node in the medical image hierarchy, the second annotation information associated with the node in the upper hierarchy, and the third annotation information associated with the node in the lower hierarchy;
acquire a new medical image to be annotated; and
input the new medical image to the annotation guide model to acquire and display annotation information of the new medical image outputted from the annotation guide model on the display unit, wherein the annotation information of the new medical image comprises a patient and a lesion associated with the new medical image.

2. The annotation support apparatus according to claim 1, wherein the processor receives designation of a region having any shape in the medical image as the designation of the finding region.

3. The annotation support apparatus according to claim 1, wherein the processor receives the input of the annotation information for the finding region, on the basis of reception of an operation of dragging and dropping an object indicating the annotation information to the finding region in the medical image displayed by the display unit.

4. The annotation support apparatus according to claim 1, wherein the processor is further configured to:
input a new training image to the annotation guide model;
acquire and display a plurality of candidate finding regions in the new training image on the display unit;
acquire and display a plurality pieces of candidate finding information associated with the plurality of candidate finding regions in the new training image on the display unit;
receive designation of one of the plurality of candidate finding regions and one of the plurality pieces of candidate finding information; and
regenerate the annotation guide model according to the new training image, patient information, the designated candidate finding region, and the designated candidate finding information of the new training image.

5. An annotation support method performed in an annotation support apparatus that supports generation of annotation information related to a medical image, wherein the medical image is managed on the basis of an attribute of each medical image by a hierarchical structure that has one medical image as a node and includes at least one of a medical image hierarchy to which the node of the medical image belongs, an upper hierarchy higher than the medical image hierarchy, or a lower hierarchy lower than the medical image hierarchy, the annotation support method comprises:

- acquiring the medical image;
- displaying the medical image;
- receiving designation of any one of the node of the medical image or a node associated with the node of the medical image in the hierarchical structure and an input of first annotation information which is information related to the designated node;
- storing the first annotation information to be associated with the designated node in the medical image hierarchy;
- receiving an input of second annotation information which is patient information indicating a patient associated with the medical image;
- storing the second annotation information to be associated with a node in the upper hierarchy;
- receiving designation of a finding region associated with a lesion in the medical image;
- receiving an input of third annotation information which is finding information indicating the finding region;
- storing the third annotation information to be associated with a node in the lower hierarchy;
- generating an annotation guide model, which receives an input medical image and outputs output annotation information related to the input medical image, with machine learning using a learning data set comprises the medical image, the first annotation information associated with the node in the medical image hierarchy, the second annotation information associated with the node in the upper hierarchy, and the third annotation information associated with the node in the lower hierarchy;
- acquiring a new medical image to be annotated;
- inputting the new medical image to the annotation guide model to acquire and display annotation information of the new medical image outputted from the annotation guide model on the display unit, wherein the annotation information of the new medical image comprises a patient and a lesion associated with the new medical image.

6. A non-transitory computer readable medium storing an annotation support program that causes a computer to function as an annotation support apparatus supporting generation of annotation information related to a medical image, wherein the medical image is managed on the basis of an attribute of each medical image by a hierarchical structure that has one medical image as a node and includes at least one of a medical image hierarchy to which the node of the medical image belongs, an upper hierarchy higher than the medical image hierarchy, or a lower hierarchy lower than the medical image hierarchy, the annotation support program causes the computer to:

- acquire the medical image;
- display the medical image;
- receive designation of any one of the node of the medical image or a node associated with the node of the medical image in the hierarchical structure and an input of first annotation information which is information related to the designated node;
- store the first annotation information to be associated with the designated node in the medical image hierarchy;
- receive an input of second annotation information which is patient information indicating a patient associated with the medical image;
- store the second annotation information to be associated with a node in the upper hierarchy;
- receive designation of a finding region associated with a lesion in the medical image;
- receive an input of third annotation information which is finding information indicating the finding region;
- store the third annotation information to be associated with a node in the lower hierarchy;
- generate an annotation guide model, which receives an input medical image and outputs output annotation information related to the input medical image, with machine learning using a learning data set comprises the medical image, the first annotation information associated with the node in the medical image hierarchy, the second annotation information associated with the node in the upper hierarchy, and the third annotation information associated with the node in the lower hierarchy;
- acquire a new medical image to be annotated; and
- input the new medical image to the annotation guide model to acquire and display annotation information of the new medical image outputted from the annotation guide model on the display unit, wherein the annotation information of the new medical image comprises a patient and a lesion associated with the new medical image.

* * * * *